US012102553B2

(12) United States Patent
Tsai et al.

(10) Patent No.: US 12,102,553 B2
(45) Date of Patent: *Oct. 1, 2024

(54) CLOSURE SYSTEM FOR A DRAINABLE POUCH

(71) Applicant: ConvaTec Technologies Inc., Las Vegas, NV (US)

(72) Inventors: Mingliang Lawrence Tsai, Holmdel, NJ (US); Tinh Nguyen-DeMary, Milltown, NJ (US)

(73) Assignee: CONVATEC TECHNOLOGIES INC., Las Vegas, NV (US)

( * ) Notice: Subject to any disclaimer, the term of this patent is extended or adjusted under 35 U.S.C. 154(b) by 1278 days.

This patent is subject to a terminal disclaimer.

(21) Appl. No.: 16/779,970

(22) Filed: Feb. 3, 2020

(65) Prior Publication Data

US 2020/0170829 A1      Jun. 4, 2020

Related U.S. Application Data

(63) Continuation of application No. 14/723,246, filed on May 27, 2015, now Pat. No. 10,588,773, which is a continuation of application No. 12/450,715, filed as application No. PCT/US2008/061212 on Apr. 23, 2008, now Pat. No. 9,066,807.

(60) Provisional application No. 60/913,723, filed on Apr. 24, 2007.

(51) Int. Cl.
*A61F 5/44*       (2006.01)
*A61F 5/445*      (2006.01)

(52) U.S. Cl.
CPC ............ *A61F 5/445* (2013.01); *A61F 5/4407* (2013.01)

(58) Field of Classification Search
CPC .............................. A61F 5/445; A61F 5/4407
See application file for complete search history.

(56) References Cited

U.S. PATENT DOCUMENTS

| 2,520,831 A | 8/1950 | Chincholl |
| 2,875,451 A | 3/1959 | Stegeman |
| 3,724,461 A | 4/1973 | Eisenberg |
| 3,825,005 A | 7/1974 | Fenton |
| 3,941,133 A | 3/1976 | Chen |
| 4,061,820 A | 12/1977 | Magid et al. |
| 4,314,558 A | 2/1982 | Korpman |

(Continued)

FOREIGN PATENT DOCUMENTS

| EP | 1378218 A1 | 1/2004 |
| GB | 2346328 A | 8/2000 |

(Continued)

OTHER PUBLICATIONS

US 10,806,622 B2, 10/2020, Hansen et al. (withdrawn)

(Continued)

*Primary Examiner* — Bradley H Philips
(74) *Attorney, Agent, or Firm* — TAFT STETTINIUS & HOLLISTER LLP; Ryan O. White; Derek B. Lavender

(57) ABSTRACT

The present invention is a drainable ostomy pouch having a closure system that includes a resealable press and seal material. The material facilitates closing and opening of the ostomy pouch outlet. A space between the comfort panel and the pouch material can accommodate the closure system or at least a portion of the closure system.

13 Claims, 2 Drawing Sheets

(56) References Cited

U.S. PATENT DOCUMENTS

| | | | |
|---|---|---|---|
| 4,519,797 A | 5/1985 | Hall | |
| 5,074,852 A | 12/1991 | Castellana et al. | |
| 5,174,659 A | 12/1992 | Laske | |
| 5,248,308 A | 9/1993 | von Emster | |
| 5,662,758 A * | 9/1997 | Hamilton | C09J 7/22 |
| | | | 156/221 |
| 5,730,736 A | 3/1998 | Sawers et al. | |
| 5,745,926 A | 5/1998 | Cailleteau | |
| 5,843,054 A | 12/1998 | Honig | |
| 5,871,607 A | 2/1999 | Hamilton et al. | |
| 5,965,235 A | 10/1999 | McGuire et al. | |
| 5,968,024 A * | 10/1999 | Freeman | A61F 5/4407 |
| | | | 604/323 |
| 6,193,918 B1 | 2/2001 | McGuire et al. | |
| 6,336,918 B1 | 1/2002 | Olsen et al. | |
| 6,421,052 B1 | 7/2002 | McGuire | |
| 6,489,022 B1 | 12/2002 | Hamilton et al. | |
| 6,589,221 B1 * | 7/2003 | Olsen | A61F 5/445 |
| | | | 604/332 |
| 6,620,474 B1 | 9/2003 | Regnier et al. | |
| 6,858,023 B2 | 2/2005 | Poulsen | |
| 7,306,581 B2 | 12/2007 | Falconer et al. | |
| 7,879,016 B2 | 2/2011 | Mandzij et al. | |
| 8,002,759 B2 | 8/2011 | Andersen et al. | |
| 8,449,513 B2 | 5/2013 | Abrams | |
| 8,979,811 B2 | 3/2015 | Keleny et al. | |
| 9,066,807 B2 | 6/2015 | Tsai et al. | |
| 9,968,480 B2 | 5/2018 | Nyberg | |
| 10,278,857 B2 | 5/2019 | Hansen et al. | |
| D862,691 S | 10/2019 | Fenton | |
| 10,434,015 B2 | 10/2019 | Taylor et al. | |
| 10,434,309 B2 | 10/2019 | Forsell | |
| 10,449,081 B2 | 10/2019 | Lee | |
| 10,449,082 B2 | 10/2019 | Johnsen | |
| 10,463,527 B2 | 11/2019 | Gallant et al. | |
| 10,470,917 B2 | 11/2019 | Chang | |
| 10,470,918 B2 | 11/2019 | Bendix | |
| 10,471,173 B2 | 11/2019 | Misawa | |
| 10,478,328 B2 | 11/2019 | Guidry et al. | |
| 10,478,329 B2 | 11/2019 | Oberholtzer et al. | |
| 10,478,330 B2 | 11/2019 | Wiltshire et al. | |
| 10,500,084 B2 | 12/2019 | Hansen et al. | |
| 10,500,315 B2 | 12/2019 | Chang et al. | |
| 10,507,318 B2 | 12/2019 | Jin et al. | |
| 10,512,562 B2 | 12/2019 | Kavanagh et al. | |
| 10,524,953 B2 | 1/2020 | Hanuka et al. | |
| 10,531,978 B2 | 1/2020 | Haas et al. | |
| 10,537,461 B2 | 1/2020 | Hanuka et al. | |
| 10,537,462 B1 | 1/2020 | Hatchett et al. | |
| 10,583,029 B2 | 3/2020 | Chang | |
| 10,588,773 B2 | 3/2020 | Tsai et al. | |
| 10,610,402 B1 | 4/2020 | Idowu et al. | |
| 10,617,554 B2 | 4/2020 | Luce | |
| 10,617,555 B2 | 4/2020 | James et al. | |
| 10,646,370 B2 | 5/2020 | Keleny et al. | |
| 10,653,551 B2 | 5/2020 | Apolinario et al. | |
| 10,660,784 B2 | 5/2020 | Nishtala et al. | |
| 10,660,785 B2 | 5/2020 | Kaufman et al. | |
| 10,660,786 B2 | 5/2020 | Obst et al. | |
| 10,729,806 B2 | 8/2020 | Bingol et al. | |
| 10,736,769 B2 | 8/2020 | Grove Sund et al. | |
| 10,744,224 B2 | 8/2020 | Israelson et al. | |
| 10,758,398 B2 | 9/2020 | Murthy Aravalli et al. | |
| 10,779,986 B2 | 9/2020 | Cox | |
| 10,799,385 B2 | 10/2020 | Hansen et al. | |
| 10,813,786 B2 | 10/2020 | Lysgaard | |
| 10,813,787 B2 | 10/2020 | Dinakara et al. | |
| 2004/0143230 A1 * | 7/2004 | Hansen | A61F 5/4404 |
| | | | 604/333 |
| 2004/0267216 A1 | 12/2004 | Udayakumar et al. | |
| 2005/0131360 A1 * | 6/2005 | Villefrance | A61F 5/445 |
| | | | 604/332 |
| 2006/0058576 A1 | 3/2006 | Davies et al. | |
| 2008/0226864 A1 | 9/2008 | Willis et al. | |
| 2009/0143755 A1 | 6/2009 | Schertiger | |
| 2010/0174253 A1 | 7/2010 | Cline et al. | |
| 2011/0218507 A1 | 9/2011 | Andersen et al. | |
| 2012/0041400 A1 | 2/2012 | Christensen | |
| 2012/0109086 A1 | 5/2012 | Tsai | |
| 2012/0136324 A1 | 5/2012 | Hanuka et al. | |
| 2012/0179124 A1 | 7/2012 | Nguyen-Demary et al. | |
| 2013/0072886 A1 | 3/2013 | Schertiger et al. | |
| 2013/0226063 A1 | 8/2013 | Taylor et al. | |
| 2014/0207094 A1 | 7/2014 | Chang | |
| 2014/0221950 A1 | 8/2014 | Chang et al. | |
| 2014/0288517 A1 | 9/2014 | Tsai et al. | |
| 2014/0316360 A1 | 10/2014 | Ekfeldt et al. | |
| 2015/0133881 A1 | 5/2015 | Freiding | |
| 2015/0209172 A1 | 7/2015 | Richmann et al. | |
| 2016/0151198 A1 | 6/2016 | Frampton et al. | |
| 2016/0193003 A1 | 7/2016 | Todd et al. | |
| 2016/0206469 A1 | 7/2016 | Prezelin | |
| 2017/0007440 A1 | 1/2017 | Moavenian | |
| 2017/0065451 A1 | 3/2017 | Brandt et al. | |
| 2017/0209295 A1 | 7/2017 | Smith et al. | |
| 2017/0209296 A1 | 7/2017 | Cailleteau | |
| 2018/0064572 A1 | 3/2018 | Wiltshire | |
| 2018/0235801 A1 | 8/2018 | Oellgaard et al. | |
| 2018/0236207 A1 | 8/2018 | Shankarsetty | |
| 2018/0303655 A1 | 10/2018 | Glithero et al. | |
| 2018/0311066 A1 | 11/2018 | Hansen et al. | |
| 2018/0344506 A1 | 12/2018 | Larsen | |
| 2018/0360644 A1 | 12/2018 | Alvarez Ponce | |
| 2018/0369474 A1 | 12/2018 | Falleboe et al. | |
| 2019/0015241 A1 | 1/2019 | Lin et al. | |
| 2019/0029868 A1 | 1/2019 | Grum-Schwensen et al. | |
| 2019/0110919 A1 | 4/2019 | Beckers et al. | |
| 2019/0117824 A1 | 4/2019 | Hansen et al. | |
| 2019/0247549 A1 | 8/2019 | Nielsen | |
| 2019/0321213 A1 | 10/2019 | Morrison, Sr. | |
| 2019/0328571 A1 | 10/2019 | Adachi | |
| 2019/0328572 A1 | 10/2019 | Weinberg et al. | |
| 2019/0358076 A1 | 11/2019 | Blatt | |
| 2019/0365560 A1 | 12/2019 | Timms et al. | |
| 2019/0374372 A1 | 12/2019 | Seres et al. | |
| 2019/0380860 A1 | 12/2019 | Eggert et al. | |
| 2019/0380861 A1 | 12/2019 | Nordquist et al. | |
| 2019/0380882 A1 | 12/2019 | Taylor et al. | |
| 2020/0000624 A1 | 1/2020 | Gibbons et al. | |
| 2020/0015996 A1 | 1/2020 | Schertiger | |
| 2020/0030134 A1 | 1/2020 | Hopper | |
| 2020/0038226 A1 | 2/2020 | Botten et al. | |
| 2020/0038227 A1 | 2/2020 | Makar, Jr. | |
| 2020/0038228 A1 | 2/2020 | Aravalli et al. | |
| 2020/0038229 A1 | 2/2020 | Aravalli | |
| 2020/0046541 A1 | 2/2020 | Sund et al. | |
| 2020/0046542 A1 | 2/2020 | Guidry et al. | |
| 2020/0046543 A1 | 2/2020 | Scalise et al. | |
| 2020/0054476 A1 | 2/2020 | Miller | |
| 2020/0054478 A1 | 2/2020 | Forsell | |
| 2020/0060863 A1 | 2/2020 | Sund et al. | |
| 2020/0061282 A1 | 2/2020 | Hvid et al. | |
| 2020/0069455 A1 | 3/2020 | Oberholtzer et al. | |
| 2020/0069529 A1 | 3/2020 | Starnes et al. | |
| 2020/0078206 A1 | 3/2020 | Chiladakis | |
| 2020/0085608 A1 | 3/2020 | Hrushka et al. | |
| 2020/0093633 A1 | 3/2020 | Blumrosen et al. | |
| 2020/0100931 A1 | 4/2020 | Schoess et al. | |
| 2020/0100946 A1 | 4/2020 | Wohlgemuth et al. | |
| 2020/0121490 A1 | 4/2020 | Woodward et al. | |
| 2020/0138618 A1 | 5/2020 | Roszkowiak et al. | |
| 2020/0138619 A1 | 5/2020 | Cisko, Jr. et al. | |
| 2020/0146944 A1 | 5/2020 | Moulton et al. | |
| 2020/0155338 A1 | 5/2020 | Meteer | |
| 2020/0163792 A1 | 5/2020 | Schertiger | |
| 2020/0164196 A1 | 5/2020 | Jin et al. | |
| 2020/0188160 A1 | 6/2020 | Udayakumar | |
| 2020/0188161 A1 | 6/2020 | Seres et al. | |
| 2020/0188162 A1 | 6/2020 | Menifee | |
| 2020/0197213 A1 | 6/2020 | Frampton-Vallance et al. | |
| 2020/0214371 A1 | 7/2020 | Apelt | |
| 2020/0214872 A1 | 7/2020 | Tretheway et al. | |
| 2020/0214873 A1 | 7/2020 | Tretheway et al. | |

(56) References Cited

U.S. PATENT DOCUMENTS

| | | |
|---|---|---|
| 2020/0214875 A1 | 7/2020 | Tretheway et al. |
| 2020/0229962 A1 | 7/2020 | Torstensen et al. |
| 2020/0237550 A1 | 7/2020 | Hussey et al. |
| 2020/0246173 A1 | 8/2020 | Schertiger et al. |
| 2020/0246174 A1 | 8/2020 | Hansen et al. |
| 2020/0246175 A1 | 8/2020 | Hansen et al. |
| 2020/0246176 A1 | 8/2020 | Hansen et al. |
| 2020/0246177 A1 | 8/2020 | Hansen et al. |
| 2020/0246178 A1 | 8/2020 | O'Hamill et al. |
| 2020/0253633 A1 | 8/2020 | Obst et al. |
| 2020/0253777 A1 | 8/2020 | Jones |
| 2020/0261254 A1 | 8/2020 | Williams et al. |
| 2020/0276044 A1 | 9/2020 | Tretheway et al. |
| 2020/0276045 A1 | 9/2020 | Bendavit |
| 2020/0281758 A1 | 9/2020 | Tan |
| 2020/0281759 A1 | 9/2020 | Lu |
| 2020/0281761 A1 | 9/2020 | Tretheway et al. |
| 2020/0289307 A1 | 9/2020 | Tretheway et al. |
| 2020/0289308 A1 | 9/2020 | Tretheway et al. |
| 2020/0297524 A1 | 9/2020 | Hunt et al. |
| 2020/0306073 A1 | 10/2020 | Olsen et al. |
| 2020/0306074 A1 | 10/2020 | Speiermann et al. |
| 2020/0330258 A1 | 10/2020 | Hansen et al. |
| 2020/0330259 A1 | 10/2020 | Sund et al. |
| 2020/0330260 A1 | 10/2020 | Hansen et al. |
| 2020/0337879 A1 | 10/2020 | Donovan et al. |
| 2020/0337880 A1 | 10/2020 | Hansen et al. |
| 2020/0337881 A1 | 10/2020 | Hansen et al. |
| 2020/0337882 A1 | 10/2020 | Hansen et al. |
| 2020/0337883 A1 | 10/2020 | Hansen et al. |
| 2020/0337884 A1 | 10/2020 | Donovan et al. |
| 2020/0337885 A1 | 10/2020 | Donovan et al. |
| 2020/0338230 A1 | 10/2020 | Israelson et al. |

FOREIGN PATENT DOCUMENTS

| | | | |
|---|---|---|---|
| GB | 2534012 | A | 7/2016 |
| GB | 2544180 | A | 5/2017 |
| GB | 2548673 | A | 9/2017 |
| GB | 2550936 | A | 12/2017 |
| GB | 2570526 | A | 7/2019 |
| GB | 2575687 | A | 1/2020 |
| GB | 2571835 | B | 2/2020 |
| WO | 2008134334 | A1 | 11/2008 |
| WO | 2015110544 | A1 | 7/2015 |
| WO | 2015138190 | A1 | 9/2015 |
| WO | 2015148035 | A1 | 10/2015 |
| WO | 2018188706 | A1 | 10/2018 |
| WO | 2018188707 | A1 | 10/2018 |
| WO | 2019058126 | A1 | 3/2019 |
| WO | 2019058127 | A1 | 3/2019 |
| WO | 2019091526 | A1 | 5/2019 |
| WO | 2019091527 | A1 | 5/2019 |
| WO | 2019091528 | A1 | 5/2019 |
| WO | 2019091529 | A1 | 5/2019 |
| WO | 2019091532 | A1 | 5/2019 |
| WO | 2019099662 | A1 | 5/2019 |
| WO | 2019120424 | A1 | 6/2019 |
| WO | 2019120429 | A1 | 6/2019 |
| WO | 2019120430 | A1 | 6/2019 |
| WO | 2019120432 | A1 | 6/2019 |
| WO | 2019120433 | A1 | 6/2019 |
| WO | 2019120434 | A1 | 6/2019 |
| WO | 2019120437 | A1 | 6/2019 |
| WO | 2019120438 | A1 | 6/2019 |
| WO | 2019120439 | A1 | 6/2019 |
| WO | 2019120442 | A1 | 6/2019 |
| WO | 2019120443 | A1 | 6/2019 |
| WO | 2019120444 | A1 | 6/2019 |
| WO | 2019120446 | A1 | 6/2019 |
| WO | 2019120448 | A1 | 6/2019 |
| WO | 2019120449 | A1 | 6/2019 |
| WO | 2019120450 | A1 | 6/2019 |
| WO | 2019120451 | A1 | 6/2019 |
| WO | 2019120452 | A1 | 6/2019 |
| WO | 2019120458 | A1 | 6/2019 |
| WO | 2019197291 | A1 | 10/2019 |
| WO | 2019197971 | A1 | 10/2019 |
| WO | 2019198012 | A1 | 10/2019 |
| WO | 2019221830 | A1 | 11/2019 |
| WO | 2019229267 | A2 | 12/2019 |
| WO | 2019229268 | A1 | 12/2019 |
| WO | 2019242828 | A1 | 12/2019 |
| WO | 2020008470 | A1 | 1/2020 |
| WO | 2020010766 | A1 | 1/2020 |
| WO | 2020014305 | A1 | 1/2020 |
| WO | 2020016471 | A1 | 1/2020 |
| WO | 2020035121 | A1 | 2/2020 |
| WO | 2020044081 | A1 | 3/2020 |
| WO | 2020055998 | A1 | 3/2020 |
| WO | 2020076607 | A1 | 4/2020 |
| WO | 2020076609 | A1 | 4/2020 |
| WO | 2020084282 | A1 | 4/2020 |
| WO | 2020125906 | A1 | 6/2020 |
| WO | 2020125907 | A1 | 6/2020 |
| WO | 2020128456 | A1 | 6/2020 |
| WO | 2020128457 | A1 | 6/2020 |
| WO | 2020156624 | A1 | 8/2020 |
| WO | 2020156625 | A1 | 8/2020 |
| WO | 2020156626 | A1 | 8/2020 |
| WO | 2020169162 | A1 | 8/2020 |
| WO | 2020173534 | A1 | 9/2020 |
| WO | 2020174218 | A1 | 9/2020 |
| WO | 2020174219 | A1 | 9/2020 |
| WO | 2020174220 | A1 | 9/2020 |
| WO | 2020174497 | A1 | 9/2020 |
| WO | 2020182923 | A1 | 9/2020 |
| WO | 2020193943 | A1 | 10/2020 |
| WO | 2020200382 | A1 | 10/2020 |
| WO | 2020201718 | A1 | 10/2020 |
| WO | 2020216426 | A1 | 10/2020 |
| WO | 2020216427 | A1 | 10/2020 |
| WO | 2020216429 | A1 | 10/2020 |
| WO | 2020219153 | A1 | 10/2020 |

OTHER PUBLICATIONS

PCT/US2008/061212 International Preliminary Report on Patentability dated Oct. 27, 2009.
PCT/US2008/061212 International Search Report and Written Opinion dated Sep. 9, 2008.
U.S. Appl. No. 12/450,715 Office Action dated Aug. 24, 2012.
U.S. Appl. No. 12/450,715 dated Dec. 5, 2011.

* cited by examiner

CLOSURE SYSTEM FOR A DRAINABLE POUCH

CROSS-REFERENCE

This application is a continuation of U.S. patent application Ser. No. 14/723,246, filed on May 27, 2015, which is a continuation of U.S. patent application Ser. No. 12/450,715, filed on Oct. 8, 2009 and issued as U.S. Pat. No. 9,066,807, which is a U.S. National Phase of PCT/US08/61212, filed Apr. 23, 2008, which claims the benefit of U.S. Provisional Application No. 60/913,723, filed on Apr. 24, 2007, each of which is incorporated in its entirety by reference.

BACKGROUND OF THE INVENTION

The present invention relates to drainable ostomy pouches for the collection of waste from a temporary or permanent ostomy opening and, more particularly, to the closure system for a drainable ostomy pouch.

The invention is applicable to a one-piece ostomy appliance in which the drainable pouch is integral with an attachment pad or wafer for attaching the drainable pouch to the body of the ostomate and with a two-piece ostomy appliance in which the pad or wafer for securing the drainable pouch to the ostomate is separate from and is releaseably attachable to the drainable pouch.

Drainable pouches include an outlet through which the pouch contents may be drained thereby enabling the pouch to be reused.

Some drainable pouches have one or more reinforcing members for controlling the cross-sectional shape of the outlet. The reinforcing members may be used to open the drainage outlet. By manually squeezing the opposite edges of the reinforcing members positioned at opposite sides of the outlet, the reinforcing member can be deformed so as to enlarge the opening. The use of these reinforcing members are described, for example, in EP1378218A1; GB2346328; and U.S. Pat. Nos. 3,825,005; 2,875,451; 5,745,926 and 3,724,461.

A drainable pouch has a body portion and a tail portion. The tail portion extends from the body portion and is tapered. The tail portion includes a recloseable outlet through which the pouch contents can drain, typically into a toilet.

Of great concern in a drainable pouch is the closure or fastening system for the outlet. Such closure systems may include a separate fastener, such as a closure clip which is removeably positioned so as to pinch closed the pouch material in the tail portion of the pouch outlet when the drainable pouch outlet is to be closed and removed when it is to be opened. Another type of fastener is an integral fastener that Is carried permanently on the pouch. A typical integral fastener utilizes mechanical engagement such as a hook and loop fastener or fasteners with mushroom tip projections.

There are concerns that arise with each of these types of fasteners. For example, a clip fastener is relatively rigid and some people find them uncomfortable to wear. The clip is also an additional, and typically, separate item which the ostomate needs to manipulate and operate when utilizing a drainable pouch. Providing a clip that suitably pinches the film together so as to prevent leakage while not opening unintentionally or cutting the pouch material and causing leakage are all additional concerns of a clip.

The hook and loop type, fastener is difficult to wipe clean and it typically as a fabric-type base that absorbs liquids and is difficult to dry when wet.

The mushroom projection type fasteners make the drainable pouch more difficult to manufacture since the fasteners require proper placement on the pouch of the strips carrying the projections. Also, the proper manner to close a drainable pouch with these projections and the complexity of the design is not readily intuitive.

Furthermore, the hook and loop fasteners and projection type fasteners are typically mounted on, a firm backing. This combination of the backing and interlocking material yields relatively rigid components. Concerns that arise include the need for manual dexterity, possible discomfort from the relatively rigid panels and/or tearing of the film by the edges of the panels.

Accordingly, objectives of the present invention include providing a closure system that is lightweight, easy to manipulate, integral with the tail, leak proof, soft and flexible, easily re-useable and intuitive.

SUMMARY OF THE INVENTION

The present invention is a drainable ostomy pouch with an integral closure system. This drainable ostomy pouch includes two panels, a front body-side panel and a rear opposing panel. The body-side panel faces the ostomate when the pouch is worn. The two panels are joined along the outer periphery of each panel in a manner so as to form a pouch with an outlet. In the body-side panel is a sternal opening. The stomal opening receives waste from the stoma of the ostomate. The waste passes through the stomal opening into the pouch. The pouch has a body portion and a tapered tail portion extending from the body portion. The outlet of the drainable pouch is in its tail portion. The drainable pouch has its contents drained through this outlet, typically into a toilet.

The tail portion of the present invention includes a closure system with a film on at least one of the two panels making up the tail portion. The film is a thin film capable of adhesively sealing against itself, referred to as self-sealing, when portions of the film are pressed together. The scaled film can be peeled apart and readily rescaled. It also functions when wet. The preferred thin film is a self-sealing adhesive coated and textured (SSAT) film developed by Procter and Gamble Company that utilizes a pressure sensitive adhesive to help the self-sealing opposing material to grip each other. This SSAT film is also covered with a multitude of bumps and depressions. The surface of this SSAT film adheres and mates in part with itself as a result of the adhesive used and the fitting of many of the hills into complimentary valleys. While it is possible that other films with an appropriate adhesive and surface topography would function well, it has been found that the press and seal technology developed by Procter and Gamble Company and marketed by The Glad Product Company as a recloseable system for food packaging works particularly well.

Patents relating to the Procter and Gamble technology include U.S. Pat. Nos. 5,662,758; 5,871,607; 5,965,235; 6,193,918; 6,421,052; and 6,489,022.

The SSAT film has a position proximate to the outlet. The SSAT film on the tail portion is foldable or rollable upon itself so as to close the outlet when the SSAT film is pressed and sealed to itself. The sealed SSAT film can be reopened to permit opening of the outlet. Accordingly, the drainable pouch outlet can be closed so the pouch can receive waste through the stomal opening and collect it in the pouch. The closure system can be opened, the pouch drained and the outlet reclosed. In this manner, accordingly, the drainable pouch can be reused.

The SSAT film is preferably on both panels of the tail portion. The SSAT film preferably covers both portions of the tail portion entirely, however, strips of SSAT film on the panels covering less than all of the tail portion may also be used. According to the present invention, strips of the closure material are preferably joined to the opposing sides of the outlet of the drainable pouch. Preferably, the width and length of the strips approximate that of the tail, although the strips can be smaller in length and/or width and still function as a closure system. It is possible to have the SSAT film on one panel of the tail portion and for the closure system to be functional, however, it is preferred to have the SSAT film on both panels.

The strips are laminated onto the tail panels. This is typically done with adhesive or by welding, with welding being the preferred manner of attachment. The material welds very well and provides a nice, relatively flat surface.

Optionally, SSAT features can be created on the surface of a commonly used pouch film, besides the possibility of a stand-alone SSAT film. For example, the ostomy film (i.e., EVA/EVA/PVdC/EVA/EVA) can be coated with self-sealing adhesives in a textured form. Other processes that can create SSAT feature on a film surface include printing and embossing.

The preferred SSAT film material has the adhesive coated textured surface on one side only and it is the side that faces outward from both of the panels of the tail.

While the prior art discusses this film technology, there is no suggestion or teaching in the prior art of laminating strips of this SSAT material or one with similar characteristics, to the opposing film panels on the tail of a drainable pouch so as to allow repeatable opening and closing of the outlet.

The drainable pouch may have a comfort layer covering at least part of the body-side panel or there may be two comfort panels covering both the body-side and rear opposing panel. Comfort panels are well known in drainable pouches.

In the drainable pouch of the present invention, the comfort layer is sealed to the body side panel and/or the rear opposing panel so as to leave an access opening between the comfort layer(s) and the panel it is covering. The access opening is preferably perpendicular to the longitudinal axis of the tail portion and proximate to where the tail portion extends from the body portion of the drainable pouch. The access opening accommodates part of the tail portion when it is folded or rolled which occurs when the outlet is closed.

The pouch may include one or more comfort panels covering the body of the pouch. The base of the comfort panel just above the tail of the drainage pouch may be left open to provide access the space between the pouch film and the comfort panel. The access opening's width is preferably at least the width of the tail portion of the pouch.

After the tail portion is folded or rolled up it may be inserted through the access opening and tucked into the space between the comfort panel and pouch material. The size of the access opening being of a width to accommodate and retain the rolled up tail. Alternatively, the SSAT film may extend from the tail portion onto the body of the pouch beneath the comfort panel. The comfort panel can be rifted to permit access to the'space or pocket by the rolled up tail portion.

When the rolled up tail portion is retained between the comfort panel and pouch material protected from unintentional unrolling. Also, the outer contour of the rolled up portion is softened by the comfort panel cover.

When the pouch is to be drained, the roiled up tail portion is removed from the pocket and unfolded. After draining, or at any time, the surface of the press and seal material can be washed relatively easily. Even when wet, the press and seal surface allows suitable closure of the tail when folded or rolled.

The drainable pouch may have reinforcing members on the tail portion proximate to the opening, with one reinforcing member on each panel of the tail portion. Reinforcing members are well known in drainable pouches and they help to facilitate opening of the outlet when the opposing ends of the reinforcing members are pushed laterally toward each other. The reinforcing members can be positioned on top of the press and seal film or the press and seal film may be located on the tail portion but not where the reinforcing members are positioned on the tail portion.

The ostomate rolls the tail up and since the material on the tail sticks to itself (adheres) and mates with itself (hills and valleys), the SSAT film seals the outlet as it is rolled up. Since the film of the pouch panels and the SSAT film on the tail portion are each thin and soft when they are rolled up, the resulting roll is relatively soft and thin. The drainable pouch may include the reinforcing members as part of the roll that can act as a guide or template for the folds or rolls.

The tail can be folded or rolled up until it reaches a designated level, such as the end of the tail.

The SSAT film avoids the need for interlocking components and the process needed for attaching the loop components. The press and seal material can be provided in rolls printed onto the pouch film to facilitate its processing into a drainage pouch having a tail with press and seal material laminated onto it.

DETAILED DESCRIPTION OF THE INVENTION

Figure 1:
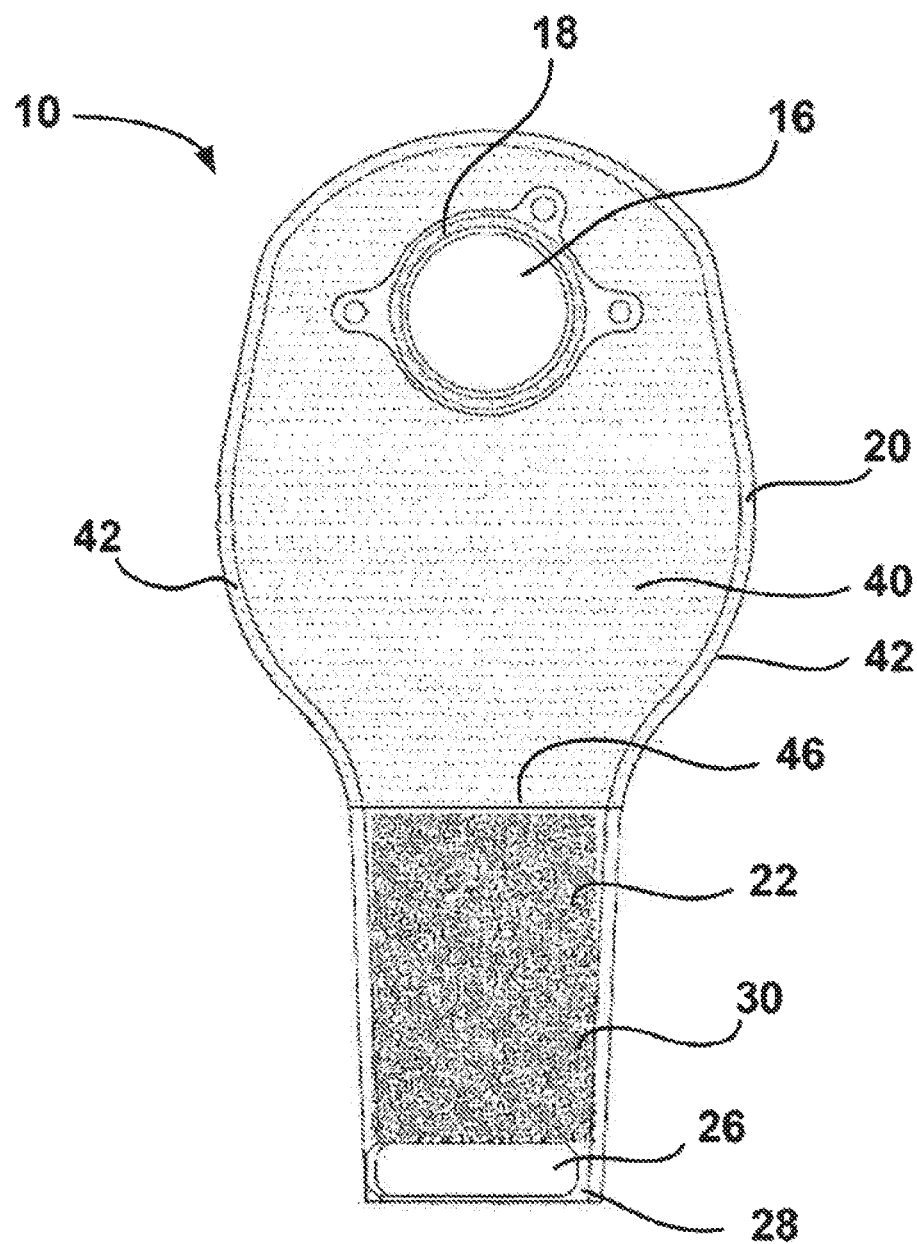
FIG. 1 is a schematic plan view of the body-side of a drainable pouch.
Figure 2:
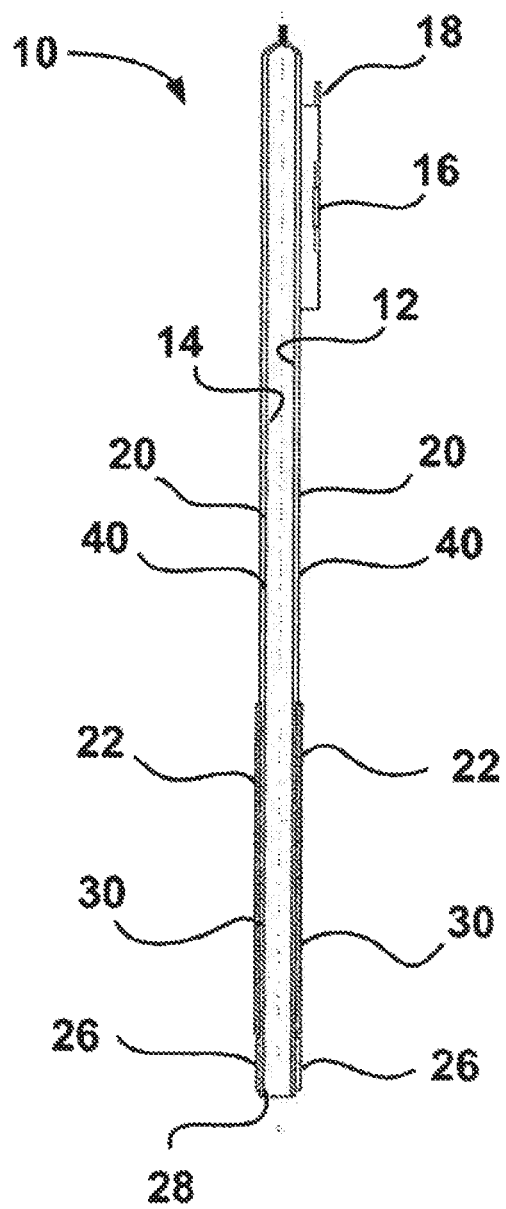
FIG. 2 is a schematic side view of the drainable pouch of FIG. 1.

Referring to FIGS. 1 and 2, wherein a drainable pouch according to the pre sent invention is generally designated by the numeral 10. This pouch 10 has a body-side pouch panel 12 and an opposite side panel 14. Each of these panels is composed of film material typically utilized for ostomy pouches, such as multiple ply film that includes layers of ethylene vinyl acetate copolymer (EVA) and polyvinylidene chloride (PVDC).

The body-side pouch panel 12 has a stomal opening 16 and is shown with mechanical coupling structure 18 surrounding the stomal opening 16. The coupling may, alternatively, be one used in an adhesive coupling system. The coupling 18 is capable of being secured to a mating coupling on the body-side wafer. It is alternatively possible for the pouch to have an adhesive wafer instead of the mechanical coupling 18 and attach directly to the wearers skin. Commonly, a hydrocolloid adhesive is used for this purpose.

The drainable ostomy pouch 10 includes a body portion 20 and a tail portion 22. The tail portion 22 is shown with a reinforcing member 26 at end 28 of the tail portion 22 on the body-side pouch panel 12 and on the opposite side panel 14.

The tail portion 22 has on its outer surface a thin film 30. This thin film is capable of self-sealing when pressed against itself. It is also capable of being peeled apart or unbonded and resealed when pressed together again. It can be wetted and dried without losing desirable adhesive properties. It can be referred to as a press and seal film with a specific type being the preferred film. The preferred thin film 30 is textured and coated with an adhesive. The texture includes hills and valleys this encourages the sealing of the film to itself. The preferred type of film was developed by Procter and Gamble Company and is sold commonly by The Glad Product Company to seal food containers. The Procter and Gamble film is described and discussed in U.S. Pat. Nos. 5,662,758; 5,871,607; 5,965,235; 6,193,918; 6,421,052; and 6,489,022 incorporated herein by reference. This preferred film has been referred to occasionally herein as SSAT film.

The thin film 30 is mounted on the outer surface of both the body-side pouch panel 12 and the opposite side panel 14. It covers the entire surface of the tail portion 22 except for where the reinforcing members 26 are secured.

The reinforcing members may be used as a template or guide when the tail portion 22 is folded or rolled up.

The body portion 20 of the pouch 10 has a comfort panel 40 covering the outer surface of the body-side pouch panel and the opposing rear side panel. The comfort panels 40 are welded along their periphery 42 to the panels 12, 14. The comfort panel 40 on the body-side pouch panel 12 lies against the skin of the wearer and is composed of material that is more comfortable to the ostomate than the pouch panel film. Comfort panels 40 may include perforations to allow air circulation and be composed of material so as to reduce potential stickiness to the ostomate due to perspiration.

The comfort panels 40 have a base 46 that is not welded or secured to the body-side pouch film 30. Accordingly, there is access to the pockets formed between the comfort panels 40 and the body portion 20. The pockets exist because the comfort panels 40 are welded to the pouch film 30 along the periphery 42 but not along the base 42.

It is also possible to utilize the thin film 30 on the tail portion 22 as a closure system by having the material only on one panel of the tail portion 22 and/or utilizing strips of the thin film 30 that do not cover the entire dimensions of the tail portion 22.

What is claimed is:

1. A drainable ostomy pouch comprising:
   a) a front body-side panel and a rear opposing panel, said panels being joined together along the outer periphery of each panel to form a pouch with an outlet, said front body-side panel including a stomal opening for receiving waste into said pouch therethrough, the pouch having a body portion and a tail portion extending therefrom, said tail portion having said outlet;
   b) said tail portion comprising:
      i) a closure system, wherein at least one of said panels comprises at least one reinforcing member located proximate to said outlet; and
      ii) an adhesive film capable of self-sealing, wherein said adhesive film is on outer surfaces of both panels of said tail portion, and wherein said adhesive film covers both panels of said tail portion substantially entirely;
   wherein said tail portion is foldable upon itself so as to resealably close said outlet.

2. The drainable ostomy pouch of claim 1, wherein said adhesive film seals to itself when pressed together in a fold and separates from itself when unfolded.

3. The drainable ostomy pouch of claim 1, wherein said adhesive film does not cover the entire dimension of the tail portion.

4. The drainable ostomy pouch of claim 3, wherein the closure system comprises strips of said adhesive film.

5. The drainable ostomy pouch of claim 1, wherein said adhesive film covers at least one panel of said tail portion substantially entirely.

6. The drainable ostomy pouch of claim 1, wherein said tail portion has a reinforcing member on each panel proximate to said outlet.

7. A drainable ostomy pouch comprising:
   a) a front body-side panel and a rear opposing panel, said panels being joined together along the outer periphery of each panel to form a pouch with an outlet, said front body-side panel including a stomal opening for receiving waste into said pouch therethrough, the pouch having a body portion and a tail portion extending therefrom, said tail portion having said outlet;
   b) said tail portion comprising:
      i) a closure system, wherein at least one of said panels comprises at least one reinforcing member located proximate to said outlet; and
      ii) an adhesive film capable of self-sealing, wherein said adhesive film is on outer surfaces of both panels of said tail portion;
   wherein said tail portion is foldable upon itself so as to resealably close said outlet;
   wherein said tail portion has a reinforcing member on each panel proximate to said outlet; and
   wherein said adhesive film covers both panels of said tail portion entirely except where said reinforcing members are attached to said pouch.

8. The drainable ostomy pouch of claim 1, wherein the adhesive film comprises hills and valleys to promote sealing of the film to itself.

9. The drainable ostomy pouch of claim 1, further comprising a comfort layer covering at least part of said front body-side panel, said comfort layer being secured to said front body-side panel in a manner so as to leave an access opening to a pocket formed between said comfort layer and front body-side panel proximate to where said tail portion extends from said body portion, said access opening accommodating at least part of said tail portion in a folded condition in the formed pocket.

10. A drainable ostomy pouch comprising:
    a) a front body-side panel and a rear opposing panel, said panels being joined together along the outer periphery of each panel to form a pouch with an outlet, said front body-side panel including a stomal opening for receiving waste into said pouch therethrough, the pouch having a body portion and a tail portion extending therefrom, said tail portion having said outlet;
    b) said tail portion comprising:
       i) a closure system, wherein at least one of said panels comprises at least one reinforcing member located proximate to said outlet; and
       ii) an adhesive film capable of self-sealing;
    wherein said tail portion is foldable upon itself so as to resealably close said outlet;
    wherein said tail portion has a reinforcing member on each panel proximate to said outlet; and
    wherein said adhesive film covers a substantial entirety of both panels of said tail portion except where said reinforcing members are attached to said pouch.

11. The drainable ostomy pouch of claim 10, wherein said adhesive film comprises hills and valleys to promote sealing of the film to itself.

12. The drainable ostomy pouch of claim 10, wherein said adhesive film is on outer surfaces of both panels of said tail portion.

13. The drainable ostomy pouch of claim 10, further comprising a comfort layer covering at least part of said front body-side panel, said comfort layer being secured to said front body-side panel in a manner so as to leave an access opening to a pocket formed between said comfort layer and front body-side panel proximate to where said tail portion extends from said body portion, said access opening accommodating at least part of said tail portion in a folded condition in the formed pocket.

* * * * *